United States Patent

Plant Pat. 3,979
Patented Nov. 16, 1976

3,979

STRAWBERRY PLANT

Royce S. Bringhurst, Davis, and Victor Voth, Santa Ana, Calif., assignors to The Regents of the University of California, Berkeley, Calif.

Filed Oct. 23, 1975, Ser. No. 625,282
Int. Cl.[2] A01H *5/03*
U.S. Cl. Plt.—49 1 Claim

This invention relates to a new and distinct variety of strawberry plant designated as "Cruz" which originated in 1965 as a cross between Cal. 37.20–45 and "Sequoia," U.S. Plant Pat. 3,178.

"Cruz" fruited first and was selected at the Wolfskill Experimental Orchards at the University of California near Davis, Calif. in 1967. At that time it was designated Cal. 65.272–104.

"Cruz" has been tested extensively at various university facilities throughout the State of California under strict control. Meristem originated, virus-negative stock has been developed at the university, asexually reproduced and multiplied.

Figure 1:
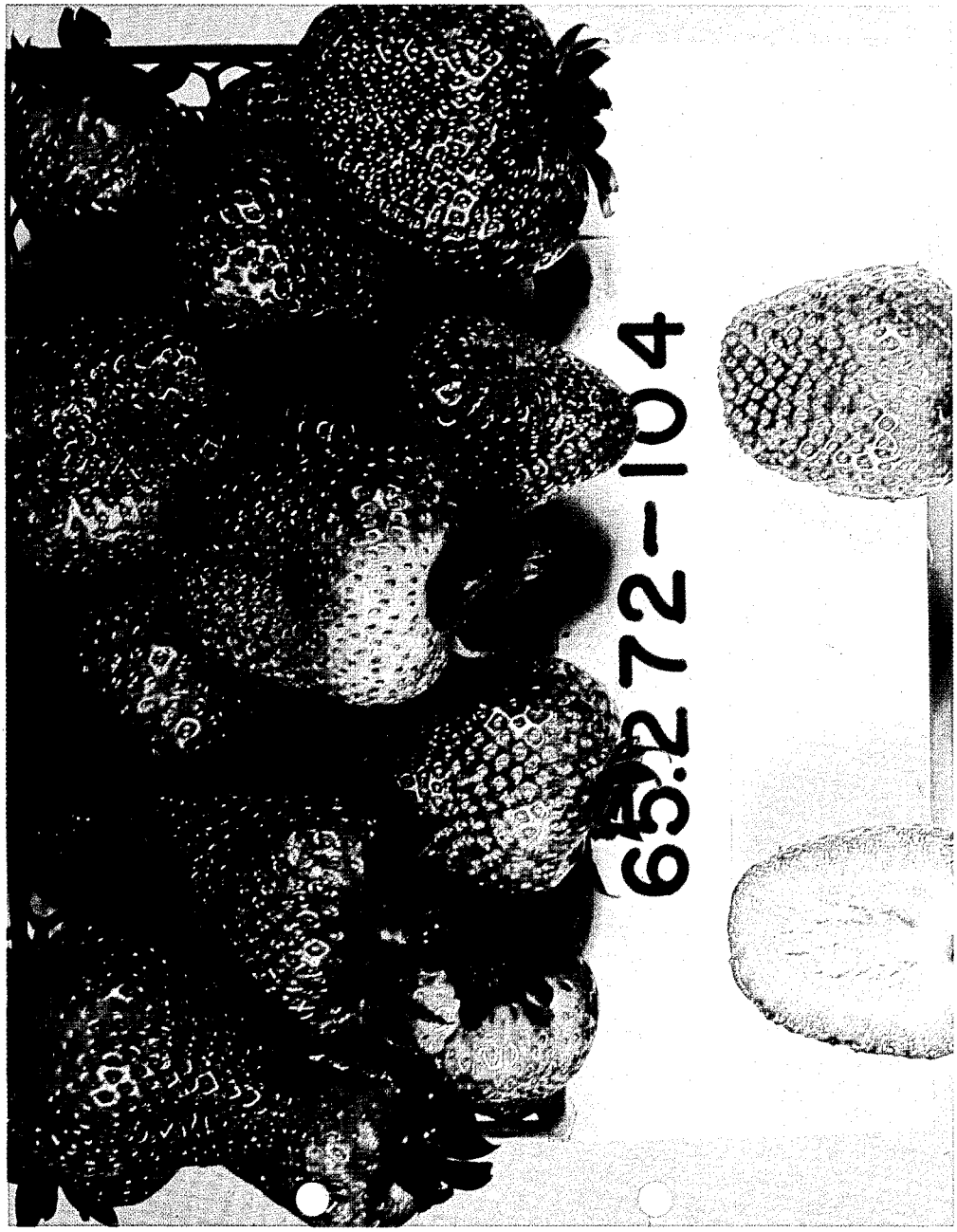
Figure 2:
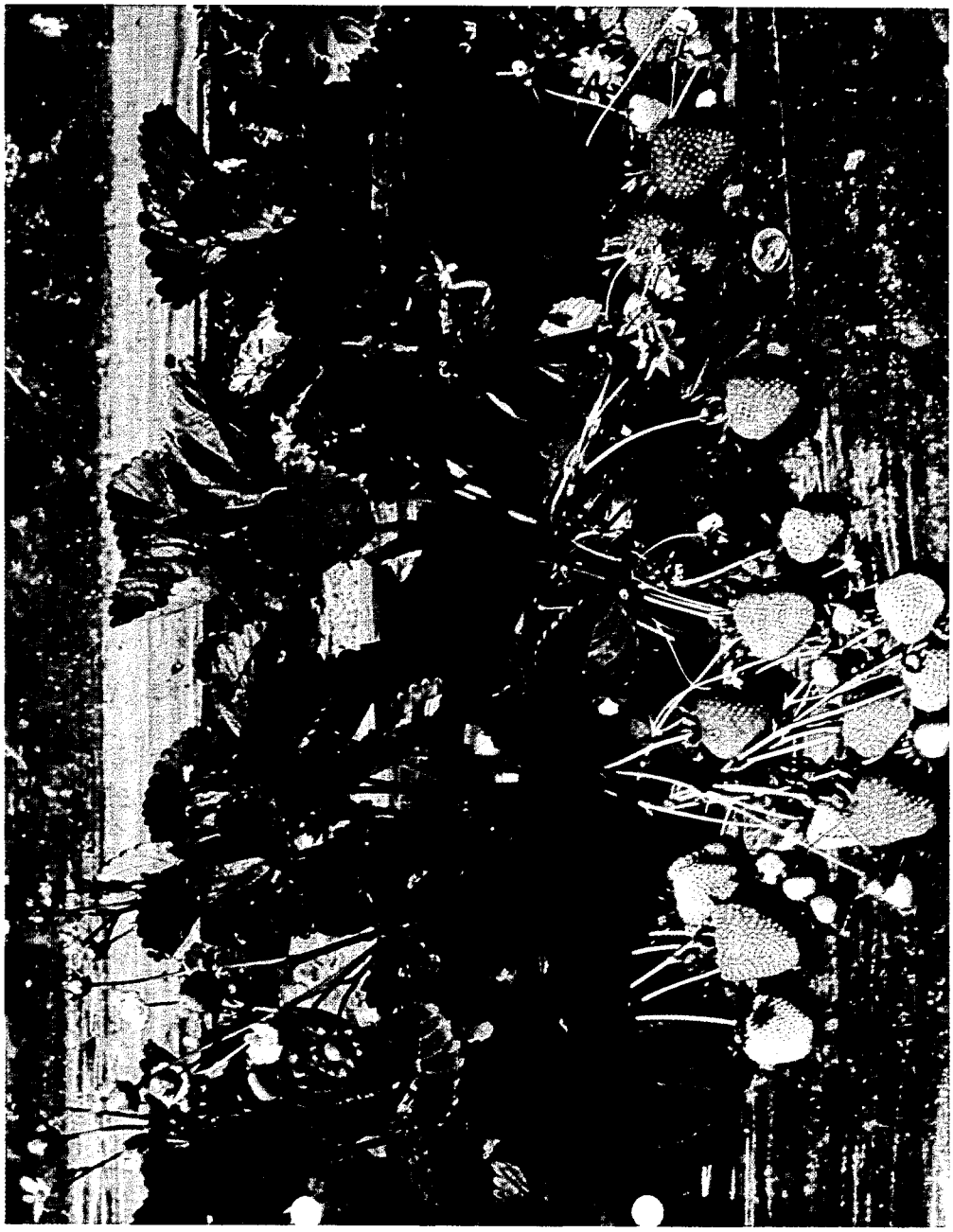

Typical plant, flower and fruit characteristics are presented in the accompanying photographic color reproductions in which FIG. 1 shows medium long conic fruit, one of which is in cross section and in which FIG. 2 shows typical springtime leaves, plant, flower and fruiting habit of winter planting in the southern areas of California.

Under optimum conditions, "Cruz" may yield quantities of fruit comparable to what should be expected from "Tioga" or "Tufts," U.S. Plant Pat. 3,561, under the winter planting system. With the summer planting system, "Cruz" yields much less than "Tioga" or "Tufts" under comparable conditions.

The dessert quality of "Cruz" fruit is excellent, definitely better than almost all the university varieties under most conditions. Soluble solids have run significantly higher for "Cruz" than for "Tioga" or "Tufts" as demonstrated by tests. "Cruz" fruit is also significantly higher in ascorbic acid (vitamin C) than "Tioga" or "Tufts" fruit, namely 83 mg./100 grams of fresh fruit as opposed to 48 mg./100 grams and 58 mg./100 grams of fresh fruit respectively of the other two cultivars. Fully ripe fruit should process well.

"Cruz" is adapted and should be useful as an interim cultivar for winter planting in coastal areas, particularly Watsonville and Salinas, Calif., planted in early to mid-October. Relatively low yield will limit its usefulness in summer planting.

The varietal characteristics of this new strawberry plant described below in detail were observed upon its discovery and subsequently through its test period.

DESCRIPTION

Plants

"Cruz" plants are medium in size, erect in habit but somewhat smaller than those of "Tioga," "Tufts" or "Sequoia." They are about as vigorous as those of "Sequoia" and require about the same amount of nitrogen fertilization. "Cruz" plants are about as tolerant of salinity as those of "Sequoia" and they are susceptible to Verticillium Wilt. "Cruz" runners prolifically and propagates about as well as "Sequoia" which is better than "Tioga."

Flowering and flowers

"Cruz" is a standard short-day type that commences flowering about with "Tioga" and "Tufts" in winter plantings. It tends to persist in fruiting longer than "Tioga" in mid-summer.

Flowers are borne on medium-long panicles, somewhat shorter than those of "Tufts" but longer than those of "Tioga." Flowers are self-fruitful with an abundance of pollen and they almost always set well.

Fruit

The medium to slightly long conic fruit is round in cross section except many of the primaries which tend to be wedged. It is seldom malformed.

The ripe color is bright, slightly orange-red that deepens to full red as the fruit matures, similar to "Tioga" and "Tufts." Internally, the color is about like that of "Tioga," and the flesh is almost as firm as that of "Tioga."

The skin is almost as tough as that of "Tioga" and it handles and ships about as well under optimum conditions. It is more susceptible to rain damage than the skin of "Tufts" or "Tioga." The achenes are about flush with the skin surface, similar to "Tioga."

"Cruz" fruit averages about as large as that of "Tufts" although the size falls off as the harvest cycle advances, similar to "Tioga."

We claim:

1. The new and distinct variety of strawberry plant herein described and illustrated, and identified by the characteristics enumerated above.

No references cited

ROBERT E. BAGWILL, Examiner